United States Patent [19]

Johansson et al.

[11] 4,044,031
[45] Aug. 23, 1977

[54] PROCESS FOR THE SEPARATION OF STEROLS

[76] Inventors: Åke Allan Johansson, Laivastokatu 4 B 23, 00160 Helsinki 16; Riitta Helena Kristiina Kivikari, Puistokaari 15 A 11, 00200 Helsinki 20; Elias Uolevi Suokas, Kimmeltie 26 D 29, 02100 Espoo 10, all of Finland

[21] Appl. No.: 702,118

[22] Filed: July 2, 1976

[51] Int. Cl.² ............................................. C07J 9/00
[52] U.S. Cl. ............................................. 260/397.25
[58] Field of Search ................................. 260/397.25

[56] References Cited

U.S. PATENT DOCUMENTS 3,335,154  8/1967  Smith ..................... 260/397.25
3,840,570  10/1974  Julian .................... 260/397.25

*Primary Examiner*—Elbert L. Roberts
*Attorney, Agent, or Firm*—Young & Thompson

[57] ABSTRACT

Process for the separation of sterols or mixtures of sterols from mixtures of unsaponifiables obtained from crude soap skimmings, soap of vegetable oil, animal fat or the like, by dissolving the mixture of unsaponifiables, extracting the polar components including the sterols into a hydrophilic solvent mixture, separating the hydrophilic phase and crystallizing the sterols from said phase by concentrating and cooling.

7 Claims, 1 Drawing Figure

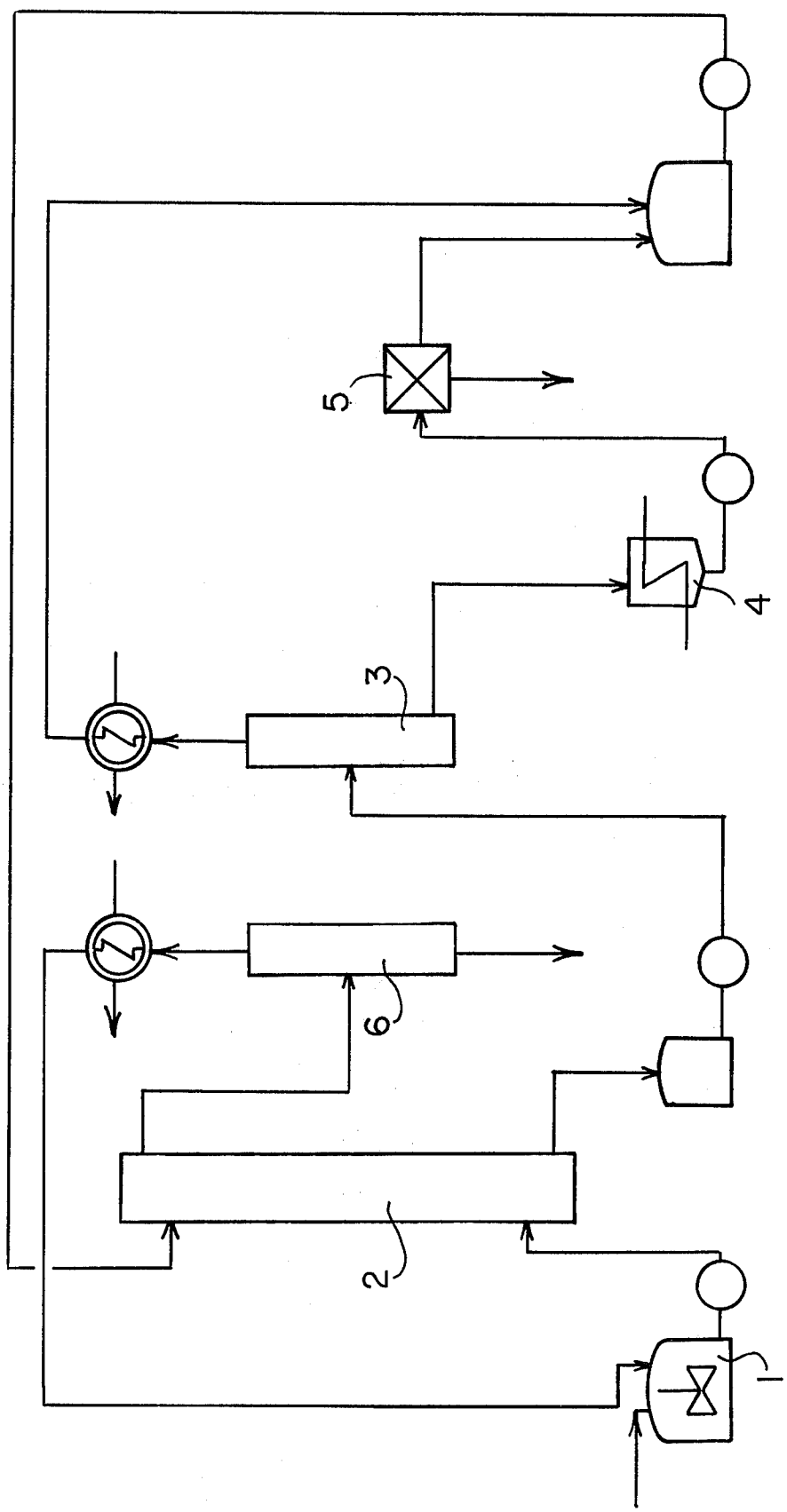

PROCESS FOR THE SEPARATION OF STEROLS

The present invention relates to a process for the separation of sterols from mixtures of unsaponifiables obtained from crude soap skimmings, soap of vegetable oil, tall oil, animal fat, or the like. Sterols make up a great portion of these unsaponifiable fractions.

In recent years much interest has been devoted to the separation of sterols from unsaponifiable fractions of different origin.

U.S. Pat. No. 3,879,431, Apr. 22, 1975, to Clark, Demars and Wilson, discloses a process for separating campesterol and sitosterol by fractional distallation. U.S. Pat. No. 2,835,682, May 20, 1958, to Steiner and Fritz, discloses a process for isolating sterols by fractionating the sterol-containing composition in a liquid, normally gaseous hydrocarbon to obtain a sterol-enriched fraction, saponificating said sterol-enriched fraction in an alcoholic alkali solution and crystallizing the sterols by adding 10 – 30% of water and cooling the mixture. U.S. Pat. No. 2,866,797, Dec. 30, 1958, to Berry, Chang, Le Bard and Miller, discloses an improved process of crystallising sterols from an ethylene dichloride solution of unsaponifiables obtained from vegetable oils, sugar cane oil and the like by adding thereto small amounts of water and methanol, in order to precipitate sterols, and recovering the sterols. U.S. Pat. No. 3,691,211, Sept. 12, 1972, to Julian, discloses a process for preparing sterols from sterol esters found in various plant sources, especially tall oil pitch, by extraction in a water-alcohol-hydrocarbon mixture followed by saponification and subsequent recrystallization and leaching.

However, no prior art process has been possible to carry out in a larger scale with good economical result. The seprated sterols are mainly used as raw materials in the pharmaceutical industry and this poses stringent requirements on the purity of the separated product. In an industrial application it is also important that the yield of the separation process is high. The unsaponifiable fractions are readily soluble in water-immiscible solvents in general and hydrocarbons and halogenated hydrocarbons in particular. However, it is not possible to separate the sterols from such solvents by concentration of the solution and fractional crystallisation, i.e., the fraction rich in sterol obtained in that way is always much too contaminated by other components present in the solution. For this reason, it is normally necessary to purify the obtained sterol crystallisate by repeated recrystallizations from one or several different solvents, such as acetone, ethanol, isopropanol, and the like. In industrial processing,, this often leads to expensive process design as well as rather low yields.

I has now been discovered that very pure sterols can be separated from the unsaponifiable fraction by employing a simple extraction involving only inexpensive common solvents, such as acetone, hexane and methanol. This process has been specifically designed to separate sterols from the betulin rich unsaponifiable fraction obtained from crude soap skimmings in a manner described in U.S. Pat. No. 3,965,085, but the method can equally well be used for the separation of sterols from unsaponifiable fractions obtained in any other way. When separating sterols from unsaponifiable fractions derived from crude soap skimmings, a particular difficulty arises from the fact that these unsaponifiable fractions have a high concentration of betulin which tends to follow the sterols throughout the separation processes. It has now been discovered that this difficulty can be overcome by the above mentioned invention. Although betulin follows the sterols into the methanol phase in the extraction, it has been discovered that under proper conditions the sterols crystallize surprisingly selectively and rather completely from the concentrated methanol solution.

Description of the new process with reference to the drawing:

The process of this invention for the recovery of sterols comprises:
1. dissolving of the unsaponifiable fraction in a suitable water-immiscible solvent, such as hexane, or a solvent mixture,
2. extraction of the polar components including the sterols from this solution into a methanol-acetone mixture to which a small amount of water has been added in order to affect phase separation,
3. concentration of this methanol-acetone solution by evaporation,
4. crystallization of the sterols from the concentrated methanol-acetone solution by cooling the solution, and
5. separation of the crystalline sterol or sterol mixture.

The non-polar fraction of the unsaponifiables can be recovered from the hexane phase by evaporating the solvents from the solution.

The sterol or sterol mixture may then, if desired, be dissolved in alcohol and recrystallized. The final step in the process is the drying operation by conventional processes.

Suitable water-immiscible solvent are hydrocarbon solvents such as hexane, heptane, xylene, and halogenated hydrocarbons, such as dichloretylene.

Suitable extraction mixtures contain 0 – 99,9% by weight of methanol, preferably 30 – 70% by weight, 0 – 50% by weight of aceton, or a slightly water-soluble solvent such as ethyl acetate, methyl ethyl ketone or the like, 0 – 50% by weight of hexane, 0.1 – 10% by weight of water, and 0 – 10% by weight of unsaponifiable other than sterols.

In a continuous extraction process, an equilibrium between the two solvent phases is established, resulting in a hexane phase containing acetone and small amounts of methanol and a methanol phase containing acetone and small amounts of hexane. Optionally, only sterols are continuously removed from the methanol phase whereby a constant concentration level of other methanol-soluble compounds will be maintained in this phase. If desired, also these components can be removed from the methanol phase by further concentrating this after the sterol crystallization.

The temperature at which the extraction is performed is not critical and may well vary between 15° and 40° C. The amount of water in the methanol phase depends on the extraction temperature, the optimum being between 0.5 and 2% by weight at room temperature.

When employing the described extraction procedure in connection with the soap extraction procedure described in U.S. Pat. No. 3,965,085 the organic phase containing the unsaponifiable components obtained from this extraction can be used as such as the hexane phase in the present invention.

The extraction process of the present invention can be performed as a continuous counter-current extraction or as a multistage batch operation.

The following examples will further illustrate the invention.

EXAMPLE 1

3.4 g of a mixture of unsaponifiables (with a β-sitosterol content of 12.5% by weight) derived from tall oil was dissolved in a solvent mixture containing 40 ml of hexane and 10 ml of acetone. The solution was extracted with a solvent mixture containing 26 ml of methanol, 8.5 ml of acetone, 15 ml of hexane, and a small amount of water (0.75 ml).

The extraction was performed in a single stage in a separatory funnel at room temperature. After separation, the methanol phase was concentrated by evaporation to half its volume. The obtained concentrate was cooled overnight to +4° C, after which the crystalline sitosterol concentrate was filtered off. The amount of dry crystalline sitosterol concentrate separated in this manner was 0.25 g, and the composition of the obtained product was 80% by weight of β-sitosterol and 20% by weight of α-sitosterol; the melting point of the product was 140° C.

EXAMPLE 2

Part 1

This part was performed in order to prepare solvent phases of an equilibrium composition. 34.7 g of unsaponifiable substance obtained from tall oil was dissolved in a solvent mixture of the following composition:

360 ml hexane
70 ml acetone
70 ml methanol

This mixture was extracted in a separatory funnel with a solvent mixture of the following composition:

200 ml hexane
90 ml acetone
210 ml methanol
5 ml water

After phase separation, the lower methanol phase was concentrated by evaporation to half its volume and cooled overnight to a temperature of +4° C. The crystalline sterol concentrate was separated by filtration. The filtrate and the solvent mixture obtained from the evaporation were combined.

The hexane phase was evaporated in order to recover the solvents.

Part 2

34.7 g of unsaponifiable substance derived from tall oil was dissolved in the hexane destillate obtained in Part 1.

The obtained mixture was extracted in a separatory funnel with the methanol phase of (filtrate and evaporated solvent) Part 1.

After phase separation, the lower methanol phase was again concentrated to half its volume by evaporation, cooled and filtered to recover the crystalline sterol concentrate.

The filtrate and the evaporated solvents were combined and used for another extraction cycle of the hexane phase of Part 2.

The procedure was repeated four times. The results obtained in this four-stage batch extraction were:

| Stage | Crystals (g) | Amount of recrystallised pure sterol concentrate (g) |
| --- | --- | --- |
| 1 | 2.0 | 0.9 |
| 2 | 1.2 | 0.6 |
| 3 | 1.1 | 0.5 |
| 4 | 0.7 | 0.3 |
|   |   | 2.3 |

(corresponds to 55 % by weight of the total amount)

EXAMPLE 3

Part 1

This part was performed to obtain solvent and raffinate phases of an equilibrium composition. A hexane phase of the following composition was prepared: 439 g of neutral substance derived from crude soap skimmings was dissolved in 4680 ml of hexane, 910 ml of acetone and 910 ml of methanol.

The total volume of the obtained hexane phase was 6.5 l.

A methanol phase with the following composition was prepared: 1680 ml of methanol, 720 ml of acetone, 1580 ml of hexane and 40 ml of water. The total volume of this mixture was 4 l.

The hexane phase was extracted with the methanol phase in a counter-current bench-scale extraction column with four sieve trays. The dimensions of the glass column were: diameter 5 cm, height 80 cm.

Both phases were fed into the column by peristaltic laboratory pumps with a flowspeed of 0.2 l/min. The methanol phase from the extraction was evaporated to half its volume, cooled and the separated crystals were filtered off. The filtrate and the solvent obtained in the evaporation were combined. The hexane phase was evaporated to dryness.

Part 2

439 g of neutral substance was dissolved in a solvent mixture obtained from the hexane phase evaporation in Part 1, to give a total liquid volume of 6.5 l.

This solution was extracted with a methanol phase obtained from Part 1 by combining the filtrate and the solvent obtained in the methanol evaporation. The extraction was performed in the same bench-scale column as described in Part 1 by keeping the hexane mixture as a continuous phase.

After extraction, the methanol phase was concentrated by evaporation to half its volume, cooled and filtered. The yield of pure β-sitosterol crystals from the above extraction was 9 g.

EXAMPLE 4

Part 1

The equilibrium phases were prepared in the same manner as described in Example 3 from the following mixtures:

1. Hexane phase: 226 g of neutral substance derived from crude soap skimmings was dissolved in 2410 ml of hexane and 470 ml of acetone and 470 ml of methanol to yield a total liquid volume of 3.350 l.
2. Methanol phase: 2510 ml of methanol, 1070 ml of acetone, 2360 ml of hexane and 60 ml of water to give a total liquid of 6 l.

Part 2

A counter-current bench-scale extraction was performed with the solutions obtained in Part 1 in the same manner as previously described. This time the methanol phase was kept as a continuous phase and the corresponding feed rations were:

methanol phase 0.2 l/min hexane phase 0.11 l/min

The methanol solution from the extraction was concentrated to half its volume, cooled and the formed sitosterol crystals were filtered off. The yield of pure sterol crystals after recrystallisation from ethanol was 21 g corresponding to a 75% by weight yield of the total amount of β-sitosterol present in the original neutral substance.

Crystalline betulin was recovered by further concentration of the betulin-rich methanol solution from which the sitosterol had been separated, by cooling and crystallizing.

EXAMPLE 5

1.2 l of a soap stock sample obtained from vegetable oil raffination was extracted according to the procedure described in U.S. Pat. No. 3,965,085. The obtained solvent phase containing the neutral substances was concentrated to a volume of 30 ml and extracted with the following solvent mixture:

20 ml methanol
20 ml hexane
10 ml acetone
0.5 ml $H_2O$

The methanol phase was concentrated by evaporation to half its volume and cooled, the crystallized sterols 0.15 g were filtered off. The sterol content in the recovered product was higher than 80% by weight. By recrystallization from ethanol a pure crystalline sterol mixture was obtained.

What we claim is:

1. A process for the separation of sterols or mixtures of sterols from mixtures of unsaponifiables obtained from crude soap skimmings, soap of vegetable oil, tall oil, animal fat or the like, comprising the steps of:
    1. dissolving the mixture of unsaponifiables in a water immiscible mixture of solvents containing
        30 - 100% by weight of hexane
        0 - 50% by weight of acetone
        0 - 50% by weight of methanol,
    2. extracting from the solution obtained the polar components including the sterols into a mixture of
        0 - 99.9% by weight of methanol
        0 - 50% by weight of hexane
        0 - 50% by weight of acetone
        0.1 - 10% by weight of water
        0 - 10% by weight of unsaponifiables other than sterols,
    3. separating the hydrophilic methanol phase,
    4. concentrating the separated hydrophilic phase by evaporation, and
    5. crystallizing the sterols by cooling the solution.

2. A continuous process for the separation of sitosterol or mixtures of sitosterols from mixtures of unsaponifiables obtained from crude soap skimmings, soap of vegetable oil, tall oil, animal fat or the like, comprising the steps of:
    1. dissolving the mixture of unsaponifiables in a water immiscible mixture of solvents containing
        60 - 95% by weight of hexane
        5 - 30% by weight of acetone
        0 - 10% by weight of methanol,
    2. extracting the solution obtained with a mixture of solvents containing
        30 - 70% by weight of methanol
        20 - 40% by weight of hexane
        10 - 30% by weight of acetone
        0.5 - 3% by weight of water
        0 - 10% by weight of unsaponifiables other than sitosterol,
    3. separating the hydrophilic methanol phase from the hydrophobic hexane phase,
    4. concentrating the separated hydrophilic phase by evaporation,
    5. crystallizing the sitosterol by cooling the solution, and
    6. separating the crystalline sitosterol, whereby in step (2) is used the hydrophilic condensate obtained when concentrating the methanol phase separated in step (4) combined with the mother liquor obtained in step (5) and in step (1) is used the hydrophobic hexane phase obtained in step (3).

3. A continuous process as claimed in claim 2, comprising the steps of
    1. dissolving the mixture of unsaponifiables in a water immiscible mixture of solvents containing
        70 - 85% by weight of hexane
        10 - 20% by weight of acetone
        3 - 10% by weight of methanol,
    2. extracting the solution obtained with a mixture of solvents containing
        35 - 50% by weight of methanol
        25 - 35% by weight of hexane
        15 - 25% by weight of acetone
        1 - 3% by weight of water
        5 - 10% by weight of unsaponifiables other than sitosterol,
    3. separating the hydrophilic methanol phase from the hydrophobic hexane phase,
    4. concentrating the separated hydrophilic phase by evaporation,
    5. crystallizing the sitosterol by cooling the solution, and
    6. separating the crystalline sitosterol, whereby in step (2) is used the hydrophilic condensate obtained when concentrating the methanol phase separated in step (4) combined with the mother liquor obtained in step (5) and in step (1) is used the hydrophobic hexane phase obtained in step (3).

4. A process as claimed in claim 3, in which the extraction step is performed at about room temperature.

5. A process as claimed in claim 3, in which hexane is substituted by a suitable hydrocarbon solvent, such as heptane, xylene, or a halogenated hydrocarbon, such as dichlorethylene.

6. A process as claimed in claim 3, in which acetone is substituted by a slightly water-soluble solvent such as ethyl acetate, methyl ethyl ketone or the like.

7. A continuous process for the separation of sitosterol or mixtures of sitosterols from mixtures of unsaponifiables obtained from crude soap skimmings or tall oil, comprising the steps of:

1. dissolving the mixture of unsaponifiables in a water immiscible mixture of solvents containing
        70 - 85% by weight of hexane
        10 - 20% by weight of acetone
        3 - 10% by weight of methanol,
    2. extracting the solution obtained with a mixture of solvents containing
        35 - 50% by weight of methanol
        25 - 35% by weight of hexane
        15 - 25% by weight of acetone
        1 - 3% by weight of water
        5 - 10% by weight of unsaponifiables other than sitosterol, 3. separating the hydrophilic methanol phase from the hydrophopic hexane phase,
4. concentrating the separated hydrophilic phase by evaporation,
5. crystallizing the sitosterol by cooling the solution, and
6. separating the crystalline sitosterol, whereby in step (2) is used the hydrophilic condensate obtained when concentrating the methanol phase separated in step (4) combined with mother liquor obtained in step (5) and in step (1) is used the hydrophobic hexane phase obtained in step (3), and whereby betulin is recovered from the mother liquor separated in step (6) by crystallizing and separating the crystalline betulin.

* * * * *